US009687312B2

(12) United States Patent
Dachs, II et al.

(10) Patent No.: US 9,687,312 B2
(45) Date of Patent: Jun. 27, 2017

(54) DETECTION PINS TO DETERMINE PRESENCE OF SURGICAL INSTRUMENT AND ADAPTER ON MANIPULATOR

(71) Applicant: Intuitive Surgical Operations, Inc., Sunnyvale, CA (US)

(72) Inventors: Gregory W. Dachs, II, San Mateo, CA (US); Bruce Michael Schena, Menlo Park, CA (US); Amir Chaghajerdi, San Jose, CA (US); Niels Smaby, Palo Alto, CA (US); Tyler Morrissette, Niantic, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/121,723

(22) PCT Filed: Mar. 17, 2015

(86) PCT No.: PCT/US2015/021020
§ 371 (c)(1),
(2) Date: Aug. 25, 2016

(87) PCT Pub. No.: WO2015/142889
PCT Pub. Date: Sep. 24, 2015

(65) Prior Publication Data
US 2016/0361127 A1    Dec. 15, 2016

Related U.S. Application Data

(60) Provisional application No. 61/954,497, filed on Mar. 17, 2014, provisional application No. 61/954,502, (Continued)

(51) Int. Cl.
*G08B 21/00*    (2006.01)
*A61B 46/10*    (2016.01)
(Continued)

(52) U.S. Cl.
CPC ........ *A61B 46/10* (2016.02); *A61B 17/00234* (2013.01); *A61B 34/30* (2016.02);
(Continued)

(58) Field of Classification Search
CPC ......... A61B 46/10; A61B 34/30; A61B 34/35; A61B 34/37; A61B 46/40; A61B 90/08;
(Continued)

(56) References Cited

U.S. PATENT DOCUMENTS 6,331,181 B1 * 12/2001 Tierney .................. G06Q 30/02
600/429
7,096,870 B2    8/2006 Lamprich et al.
(Continued)

FOREIGN PATENT DOCUMENTS

EP          1862123 A2      12/2007
KR       20110032444 A       3/2011
(Continued)

OTHER PUBLICATIONS

International Search Report and Written Opinion for Application No. PCT/US15/21111, mailed on May 21, 2015, 10 pages.
(Continued)

*Primary Examiner* — Kerri McNally
(74) *Attorney, Agent, or Firm* — Blakely Sokoloff Taylor & Zafman LLP

(57) ABSTRACT

An instrument carriage provides control of a surgical instrument coupled to the instrument carriage. The instrument carriage includes a control surface that is coupled to the surgical instrument to provide the control. A detection pin having a first proximal end that extends from the control surface is coupled to the instrument carriage. A magnet is fixed to a distal end of the detection pin. A carriage controller provides an indication that the surgical instrument is coupled to the instrument carriage when movement of the detection
(Continued)

pin causes an output signal from a Hall effect sensor to exceed a threshold value that is stored in the carriage controller as part of a calibration procedure during the assembly of the instrument carriage. Surgical instrument removal may be indicated when detection pin movement causes the output signal to be less than an instrument removal threshold value of less than the instrument threshold value.

18 Claims, 8 Drawing Sheets

Related U.S. Application Data filed on Mar. 17, 2014, provisional application No. 61/954,557, filed on Mar. 17, 2014, provisional application No. 61/954,571, filed on Mar. 17, 2014, provisional application No. 61/954,595, filed on Mar. 17, 2014, provisional application No. 62/019,318, filed on Jun. 30, 2014, provisional application No. 62/103,991, filed on Jan. 15, 2015, provisional application No. 62/104,306, filed on Jan. 16, 2015.

(51) Int. Cl.
*A61B 90/00* (2016.01)
*A61B 34/30* (2016.01)
*A61B 34/37* (2016.01)
*A61B 34/35* (2016.01)
*A61B 46/00* (2016.01)
*A61B 90/98* (2016.01)
*A61B 17/00* (2006.01)
*F16H 1/20* (2006.01)

(52) U.S. Cl.
CPC ............ *A61B 34/35* (2016.02); *A61B 34/37* (2016.02); *A61B 46/40* (2016.02); *A61B 90/08* (2016.02); *A61B 90/361* (2016.02); *A61B 90/98* (2016.02); *A61B 2017/00477* (2013.01); *A61B 2090/0813* (2016.02); *F16H 1/20* (2013.01); *Y10T 29/49817* (2015.01); *Y10T 403/59* (2015.01)

(58) Field of Classification Search
CPC .. A61B 90/361; A61B 90/98; A61B 17/00234
USPC ...................................................... 340/686.1
See application file for complete search history.

(56) References Cited

U.S. PATENT DOCUMENTS

| | | | |
|---|---|---|---|
| 7,758,569 | B2 | 7/2010 | Brock |
| 7,947,050 | B2 | 5/2011 | Lee et al. |
| 8,220,468 | B2 | 7/2012 | Cooper et al. |
| 8,506,555 | B2 | 8/2013 | Ruiz Morales |
| 2002/0111635 | A1* | 8/2002 | Jensen .................. B25J 3/04 606/130 |
| 2004/0049205 | A1 | 3/2004 | Lee et al. |
| 2005/0240178 | A1 | 10/2005 | Morley et al. |
| 2006/0235436 | A1 | 10/2006 | Anderson et al. |
| 2007/0119274 | A1 | 5/2007 | Devengenzo et al. |
| 2008/0103491 | A1 | 5/2008 | Omori et al. |
| 2008/0140088 | A1 | 6/2008 | Orban, III |
| 2010/0163057 | A1 | 7/2010 | Anderson et al. |
| 2010/0170519 | A1 | 7/2010 | Romo et al. |
| 2011/0084113 | A1 | 4/2011 | Bedi et al. |
| 2011/0118754 | A1 | 5/2011 | Dachs, II et al. |
| 2011/0288560 | A1 | 11/2011 | Shohat et al. |
| 2011/0290855 | A1 | 12/2011 | Moore et al. |
| 2011/0295270 | A1 | 12/2011 | Giordano et al. |
| 2012/0197094 | A1 | 8/2012 | Zhang et al. |
| 2012/0239060 | A1 | 9/2012 | Orban, III |
| 2012/0247489 | A1 | 10/2012 | Orban, III et al. |
| 2012/0292367 | A1 | 11/2012 | Morgan et al. |
| 2013/0110129 | A1 | 5/2013 | Reid et al. |
| 2013/0211397 | A1 | 8/2013 | Parihar et al. |
| 2013/0325034 | A1 | 12/2013 | Schena et al. |
| 2013/0331858 | A1* | 12/2013 | Devengenzo .......... A61B 90/00 606/130 |
| 2014/0001234 | A1 | 1/2014 | Shelton, IV et al. |
| 2014/0069437 | A1 | 3/2014 | Reis et al. |
| 2015/0257841 | A1 | 9/2015 | Dachs, II |
| 2015/0257842 | A1 | 9/2015 | Dachs, II |
| 2016/0354173 | A1 | 12/2016 | Dachs, II et al. |
| 2016/0361049 | A1 | 12/2016 | Dachs, II et al. |
| 2016/0361124 | A1 | 12/2016 | Dachs, II et al. |
| 2016/0361126 | A1 | 12/2016 | Schena et al. |
| 2016/0361129 | A1 | 12/2016 | Morrissette et al. |
| 2016/0361131 | A1 | 12/2016 | Dachs, II et al. |
| 2016/0367328 | A1 | 12/2016 | Dachs, II et al. |

FOREIGN PATENT DOCUMENTS

| | | |
|---|---|---|
| KR | 20130080638 A | 7/2013 |
| KR | 20130120316 A | 11/2013 |
| WO | WO-2007075864 A1 | 7/2007 |
| WO | WO-2009151205 A1 | 12/2009 |
| WO | WO-2011037394 A2 | 3/2011 |
| WO | WO-2011143016 A1 | 11/2011 |

OTHER PUBLICATIONS

International Search Report and Written Opinion for Application No. PCT/US15/20880, mailed on Jul. 14, 2015, 9 pages.
International Search Report and Written Opinion for Application No. PCT/US15/20882, mailed on May 29, 2015, 14 pages.
International Search Report and Written Opinion for Application No. PCT/US15/20884, mailed on Jun. 12, 2015, 13 pages.
International Search Report and Written Opinion for Application No. PCT/US15/20886, mailed on Jun. 4, 2015, 19 pages.
International Search Report and Written Opinion for Application No. PCT/US15/20876, mailed on Jun. 12, 2015, 17 pages.
International Search Report and Written Opinion for Application No. PCT/US15/20885, mailed on Jun. 5, 2015, 7 pages.
International Search Report and Written Opinion for Application No. PCT/US15/20888, mailed on Jun. 5, 2015, 9 pages.
International Search Report and Written Opinion for Application No. PCT/US15/21020, mailed on Jun. 5, 2015, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

DETECTION PINS TO DETERMINE PRESENCE OF SURGICAL INSTRUMENT AND ADAPTER ON MANIPULATOR

This application is a 371 of international application number PCT/US15/021020 filed Mar. 17, 2015, and claims benefit of the following earlier filed applications:

| | | |
|---|---|---|
| U.S. | 61/954,497 | 17 Mar. 2014 (17-03-2014) |
| U.S. | 61/954,502 | 17 Mar. 2014 (17-03-2014) |
| U.S. | 61/954,557 | 17 Mar. 2014 (17-03-2014) |
| U.S. | 61/954,571 | 17 Mar. 2014 (17-03-2014) |
| U.S. | 61/954,595 | 17 Mar. 2014 (17-03-2014) |
| U.S. | 62/019,318 | 30 Jun. 2014 (30-06-2014) |
| U.S. | 62/103,991 | 15 Jan. 2015 (15-01-2015) |
| U.S. | 62/104,306 | 16 Jan. 2015 (16-01-2015) |

Each of these applications is specifically incorporated herein by reference to the greatest extent permitted.

FIELD

Embodiments of the invention relate to the field of surgical instrument adapters; and more specifically, to detection pins for determining presence of surgical instruments and instrument adapters on teleoperated manipulators.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the end effector, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

Performing surgery with teleoperated surgical instruments creates new challenges. One challenge is the need to maintain the region adjacent the patient in a sterile condition. However, the motors, sensors, encoders and electrical connections that are necessary to control the surgical instruments typically cannot be sterilized using conventional methods, e.g., steam, heat and pressure or chemicals, because they would be damaged or destroyed in the sterilization process.

Another challenge with teleoperated surgery systems is that a number of connections are required between the surgical instrument and the teleoperated actuator and its controller. Connections are required to transmit the actuator forces, electrical signals, and data. This makes the attachment of the surgical instrument to the teleoperated actuator and its controller complex.

Still another challenge with teleoperated actuated teleoperated surgery systems is that an operating room is not an ideal environment for preparing precision mechanical assemblies.

It would be desirable to provide a way of determining if a sterile adapter and/or a surgical instrument is present on a teleoperated manipulator.

SUMMARY

A teleoperated actuated surgical system includes a surgical instrument, a teleoperated actuated surgical instrument manipulator, and an instrument sterile adapter (ISA). The ISA is placed between the coupling of the surgical instrument and the teleoperated actuated surgical instrument manipulator in order to provide a sterile coupling point when there is a need to exchange one surgical instrument for another. A carriage portion of the teleoperated actuated surgical instrument manipulator includes a plurality of detection pins used to detection the presence of the ISA and a surgical instrument.

Herein, the disclosure provides embodiments pertaining to reliably detecting the engagement of the ISA with the teleoperated actuated surgical instrument manipulator and the engagement of the surgical instrument with the ISA. Additionally, one or more of the embodiments accomplishes the reliable detection of both engagements using one mechanism (e.g., a plurality of detection pins and corresponding sensors). In one embodiment, a first set of one or more detection pins may be used to detect the presence of the ISA while a second set of one or more detection pins may be used to detect the presence of the surgical instrument. Alternatively, the first set of one or more detection pins may be used to detect the presence of both the ISA and the surgical instrument.

In one embodiment, the detection of the presence of the ISA may be accomplished by determining the distance between an analog Hall effect sensor and a magnet attached to a proximal end of a detection pin. When the distance between the analog Hall effect sensor and a face of the magnet is within a first range, the analog Hall effect sensor may output a first predetermined voltage identifying the presence of the ISA. In addition, the output of the first predetermined voltage may signify the engagement of the ISA with the carriage of the teleoperated actuated surgical instrument manipulator. When the distance between the analog Hall effect sensor and the face of the magnet is within a second range being smaller than the first range, the analog Hall effect sensor may output a second predetermined voltage identifying the presence of the surgical instrument. Additionally, the output of the second predetermined voltage may signify the engagement of the surgical instrument with the ISA. Other features and advantages of the present invention will be apparent from the accompanying drawings and from the detailed description that follows below.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DESCRIPTION OF EMBODIMENTS

Figure 1:
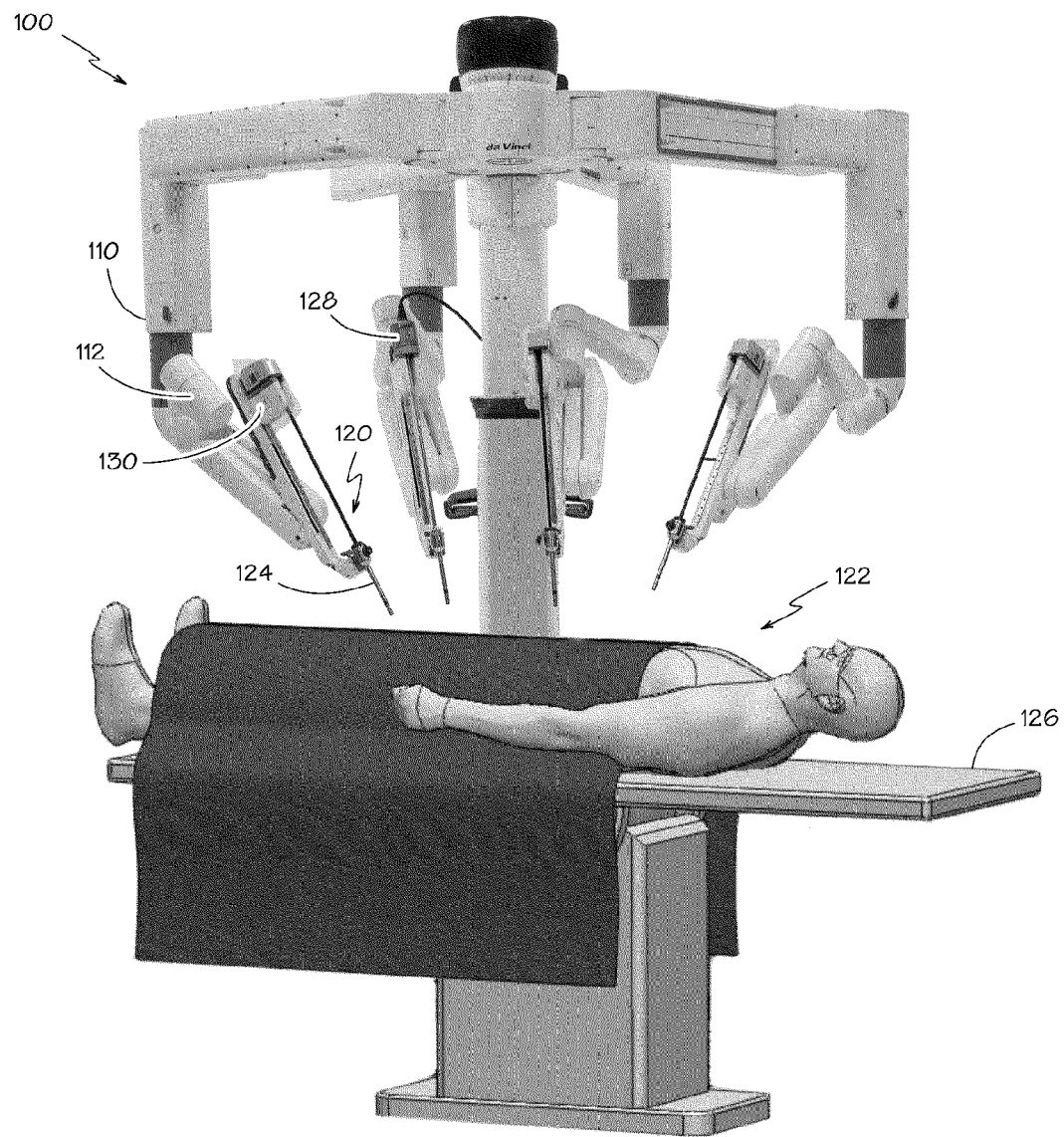
FIG. 1 is a simplified perspective view of a teleoperated actuated surgical system with a teleoperated controlled surgical instrument inserted through a port in a patient's abdomen.

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The term "object" generally refers to a component or group of components. For example, an object may refer to either a pocket or a boss of a disk within the specification or claims. Throughout the specification and claims, the terms "object", "component", "portion", "part", and "piece" are used interchangeably.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four manipulators 112, more or fewer manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 112 to move its associated surgical instrument around a center of motion on the instrument that stays stationary with reference to the patient, and this center of motion is typically located to be at the position where the instrument enters the body.

The term "surgical instrument" is used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the proximal end of the camera instrument 128 to one or more imaging sensors (e.g., CCD or CMOS sensors) outside of the patient's body 122. Alternatively, the imaging sensor(s) may be positioned at the proximal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the proximal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
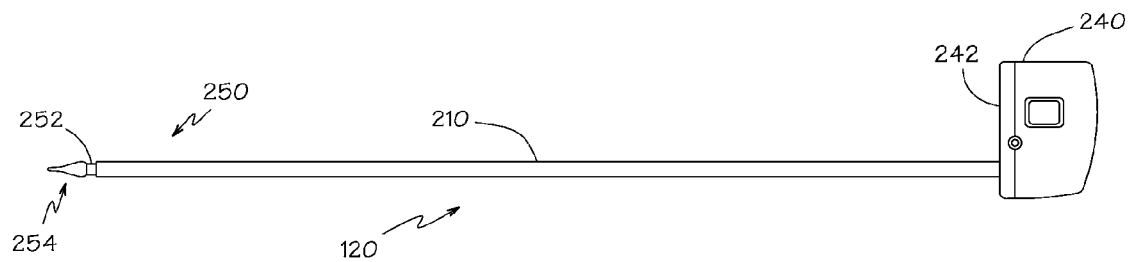
FIG. 2 is a plan view of a surgical instrument for use with a teleoperated actuator.

FIG. 2 is a side view of an illustrative embodiment of the surgical instrument 120, comprising a proximal portion 250 and a distal control mechanism 240 coupled by an elongate tube 210. The proximal portion 250 of the surgical instrument 120 may provide any of a variety of end effectors such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the end effector 254 is coupled to the elongate tube 210 by a "wrist" 252 that allows the orientation of the end effector to be manipulated with reference to the instrument tube 210.

Figure 3A:
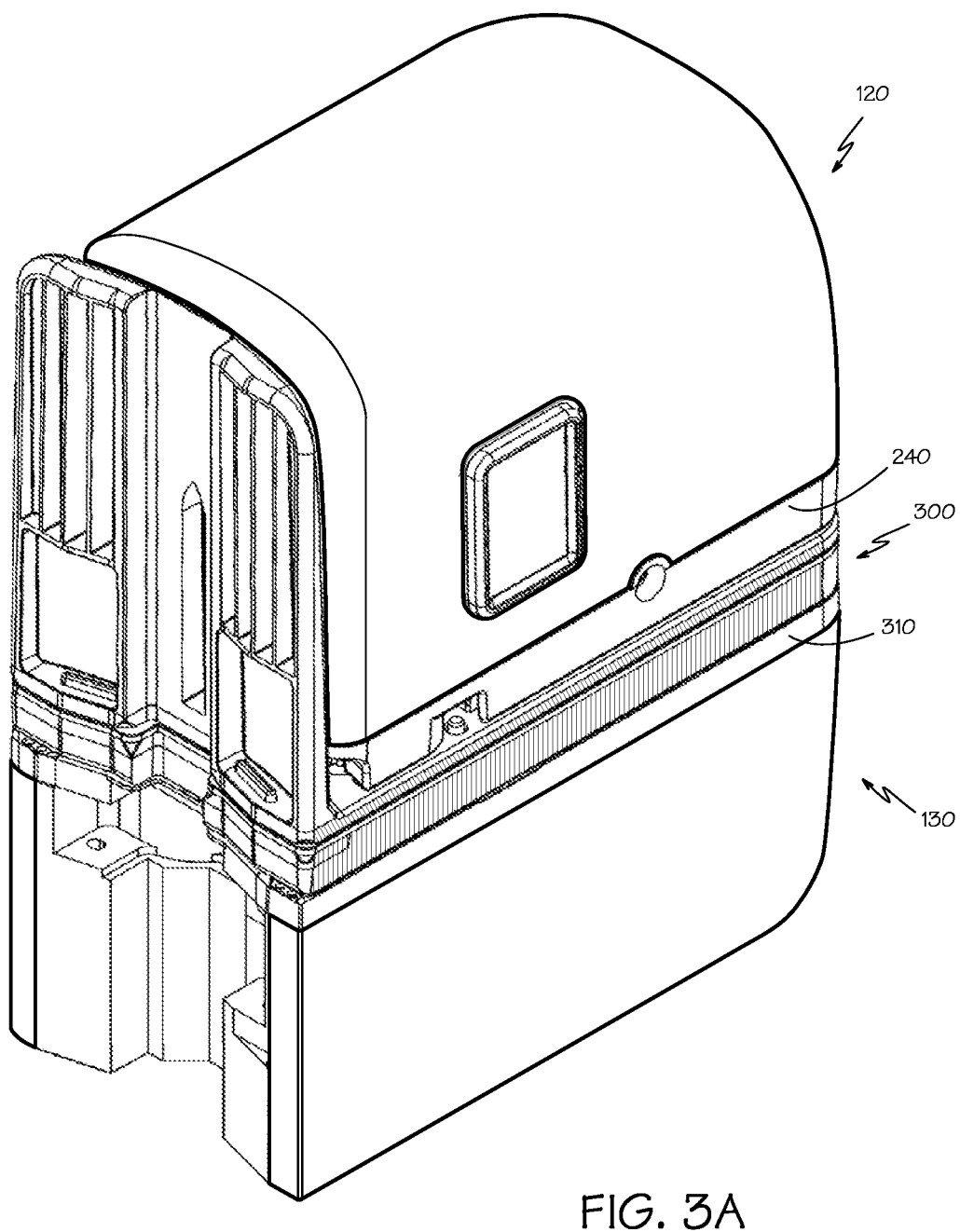
FIG. 3A is an illustration of an exemplary embodiment of a coupling of a surgical instrument, a carriage of a teleoperated actuated surgical instrument manipulator and an instrument sterile adapter (ISA).

Referring to FIG. 3A, an exemplary embodiment of a surgical instrument 120, a control surface 310 of a teleoperated actuated surgical instrument carriage 130 and an instrument sterile adapter (ISA) 300 illustrated in a coupled condition is shown. The control surface 310 is coupled to the surgical instrument 120 to provide control of the surgical instrument. The ISA 300 extends the control surface 310 of the instrument carriage 130 to provide a disposable sterile equivalent of the control surface that is in direct contact with the surgical instrument 120.

Figure 3B:
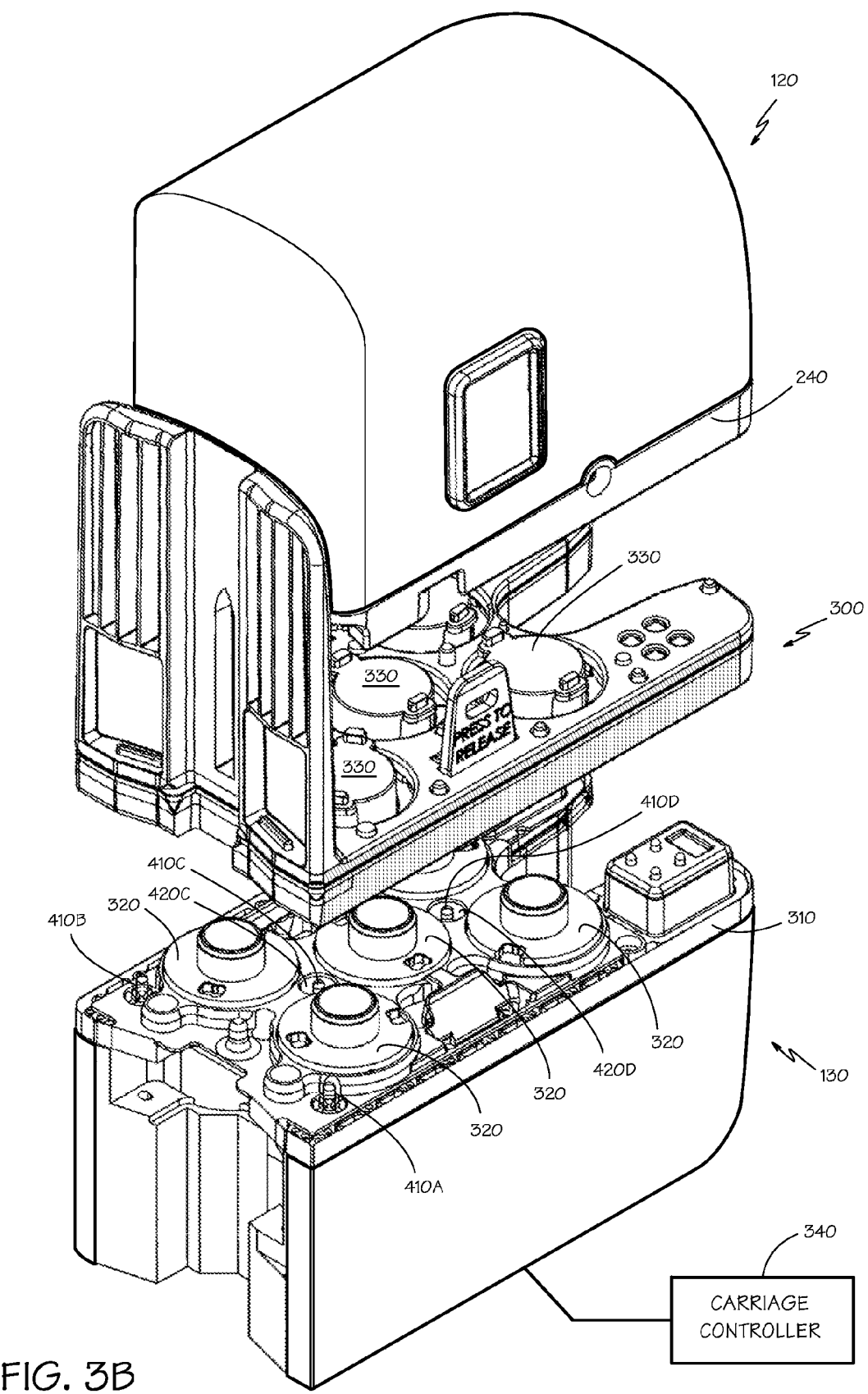
FIG. 3B is an illustration of the coupler system of FIG. 3A with the parts separated.

Referring to FIG. 3B, an exemplary embodiment of the coupler system of FIG. 3A is provided. In the first stage of the coupling process, the underside of the ISA 300 is coupled with the control surface 310 on the topside of the carriage 130. Specifically, the carriage drivers 320 mate with the underside of the corresponding ISA couplers 330. Next, the surgical instrument 120 is coupled with the topside of the ISA 300. The topside of the ISA couplers 330 mate with corresponding instrument drivers (not shown).

However, the addition of an ISA 300 between the coupling of the surgical instrument 120 and the teleoperated actuated surgical instrument carriage 130 creates a need to determine if the instrument sterile adapter is present and properly engaged with the teleoperated actuated surgical instrument carriage 130. Similarly, there is a need to determine if the surgical instrument 120 is present and properly engaged with the instrument sterile adapter 300.

Installation of an Instrument Sterile Adapter and Surgical Instrument

Figure 4:
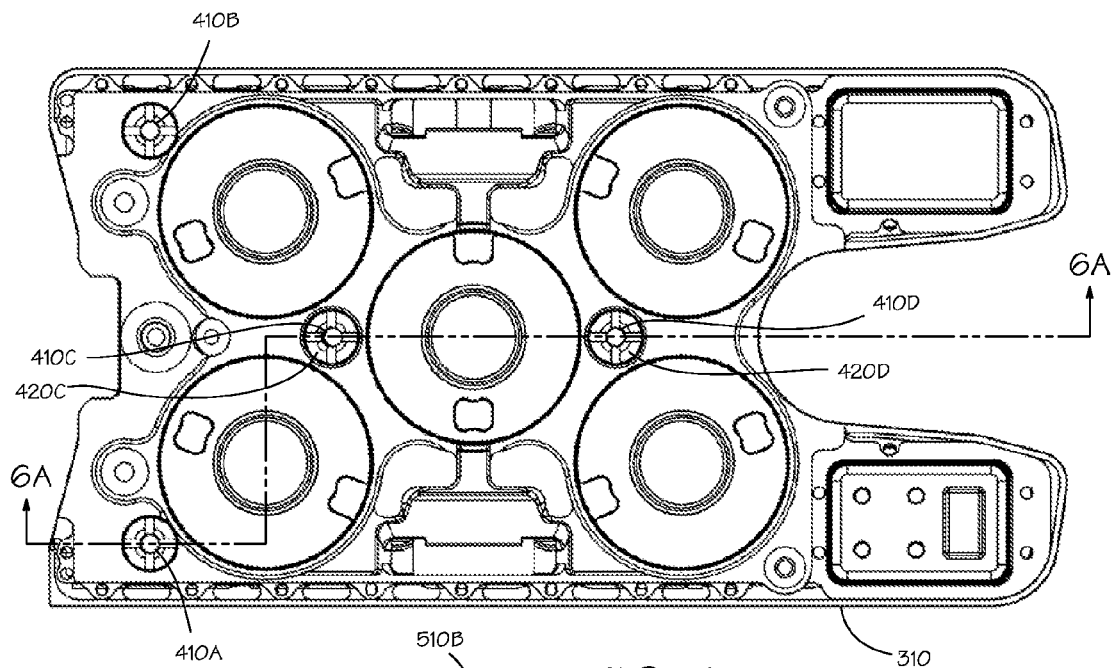
FIG. 4 is an illustration of an exemplary embodiment of a control surface of the carriage of FIG. 1 from a top-down perspective including a plurality of the detection pins.

Referring to FIG. 4, an exemplary embodiment of a control surface 310 of the carriage 130 from a top perspective including detection pins 410A-410D is shown. The detection pins 410A-410D are shown in one configuration; however, in other embodiments, the detection pins 410A-410D may be provided in other configurations as would be recognized by one of ordinary skill in the art.

Figure 5:
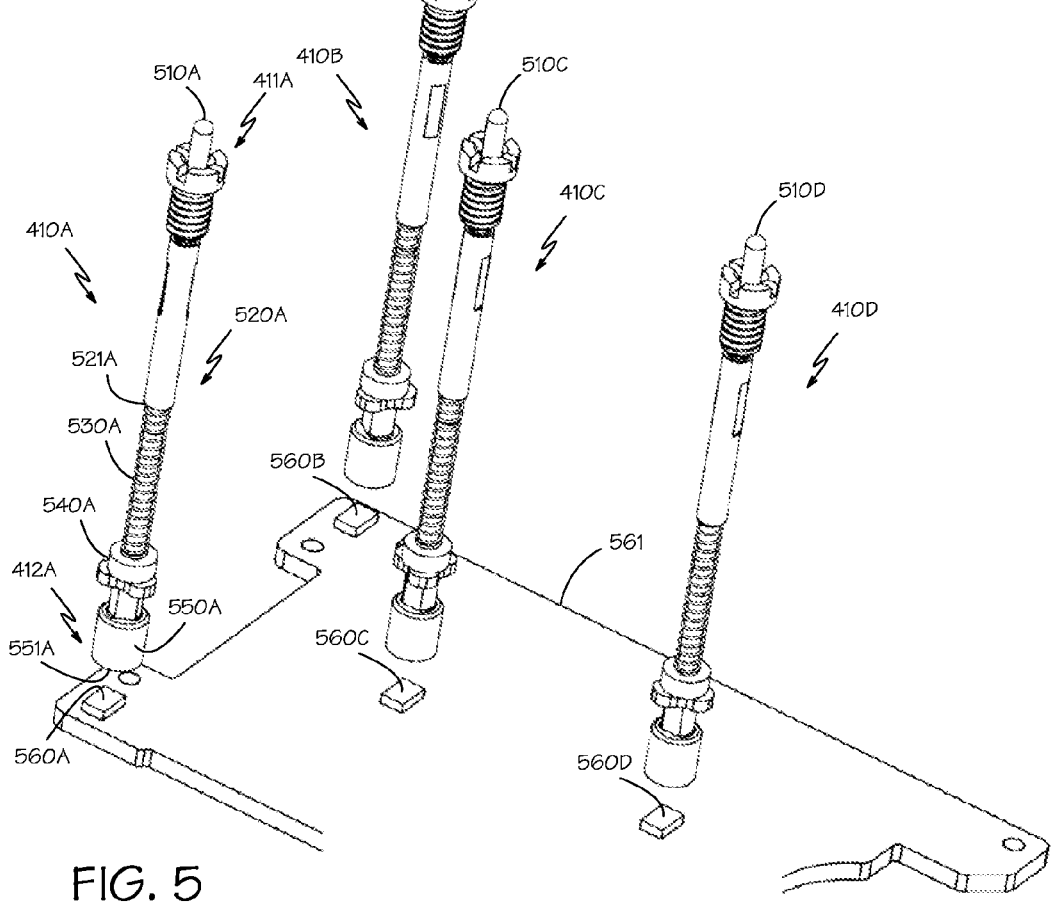
FIG. 5 is an illustration of an exemplary embodiment of the detection pins relative to the circuit board 561 and the sensors.

Referring to FIG. 5, an illustration of an exemplary embodiment of the detection pins 410A-410D relative to the circuit board 561 and the sensors 560A-560D is shown. The detection pin 410A includes the distal end 411A with a sensing tip 510A, the proximal end 412A, a shaft 520A, a shoulder 521A of the shaft 520A, a spring 530A, an upstop 540A and a magnet housing 550A. The magnet housing 550A includes a magnet having a magnet face 551A, which faces the sensor 560A. Each of the detection pins 410B-410D include the same components as 410A.

The shaft 520A and the magnet housing 550A move as a single assembly within the upstop 540A and the distal end 411A bushing. The upstop 540A limits the upward travel of the shaft 520A and the magnet housing 550A at the point where a larger diameter of the shaft 520A at the proximal end 412A is unable to pass through the upstop.

The spring 530A is captive between the upstop 540A and the shoulder 521A of the shaft 520A. As a result, the spring 530A urges the shaft 520A upwardly toward the distal end 411A. A downward force can be applied to the distal end 411A of the shaft 520A to move the shaft and the attached magnet housing 550A toward the sensor 560A. The distal end 411C-411D of the detection pin 410C-410D may be wholly or partially contained in a carriage well 420C-420D (better seen in FIG. 6A) that protects the detection pin from application of sideward forces that could damage the detection pin.

Figure 6A:
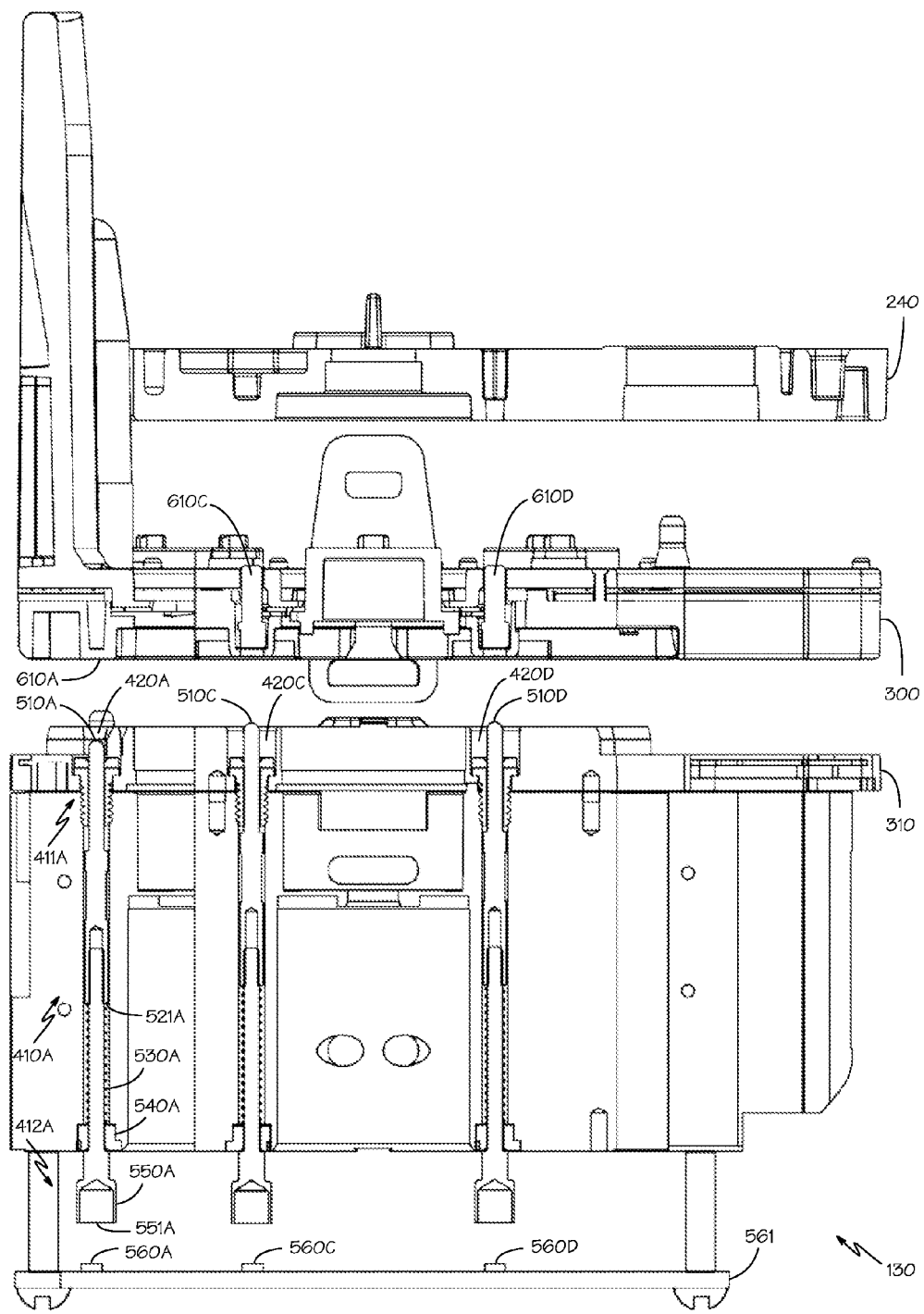
FIG. 6A is a sectional illustration of the plurality of detection pins of the carriage of FIG. 4 relative to the surgical instrument, the ISA and the circuit board prior the engagement of the ISA with the carriage taken along section line 6A-6A in FIG. 4.
Figure 6B:
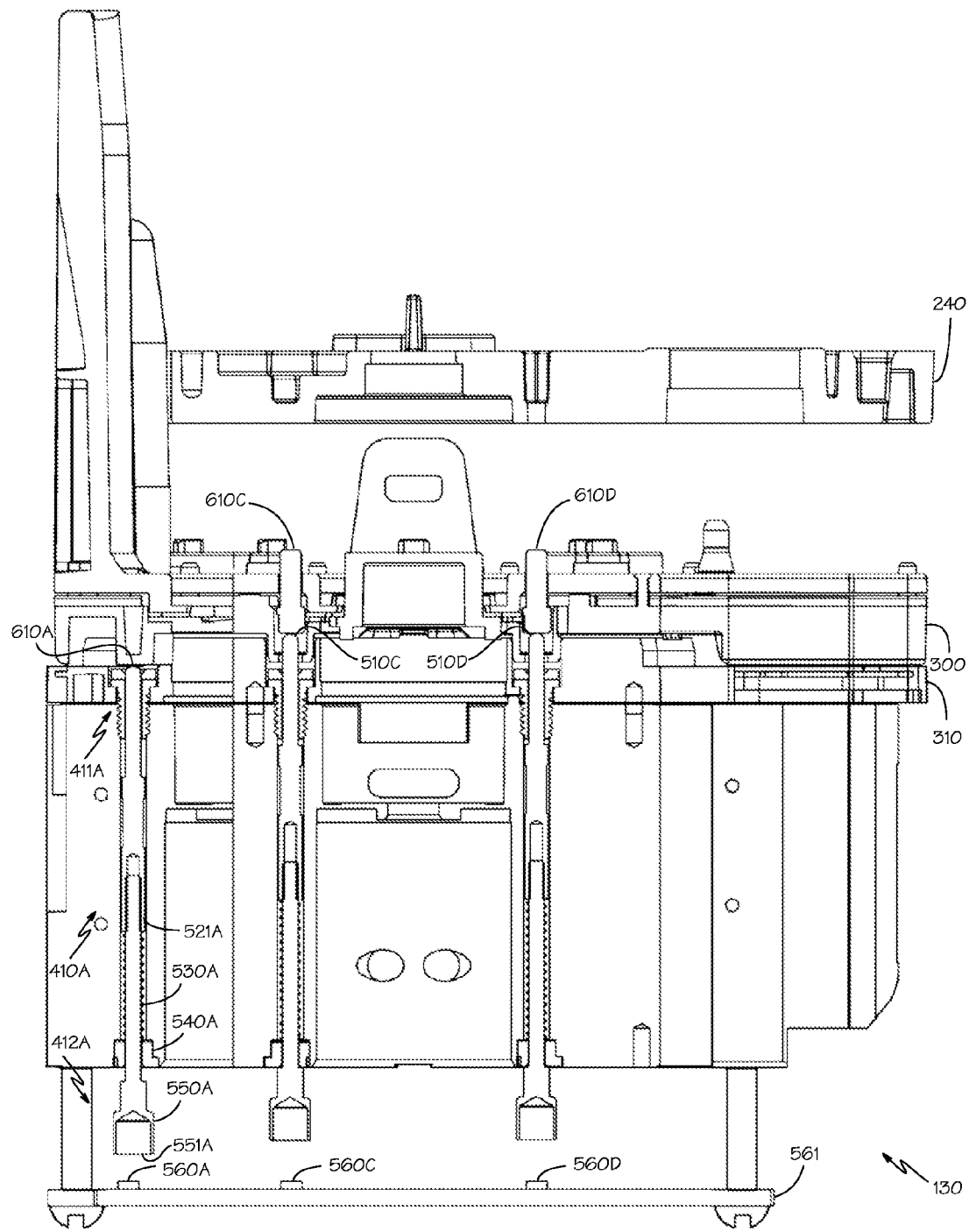
FIG. 6B is a sectional of the plurality of detection pins of the carriage of FIG. 4 relative to the ISA and the circuit board upon the engagement of the ISA with the carriage taken along section line 6A-6A in FIG. 4.
Figure 6C:
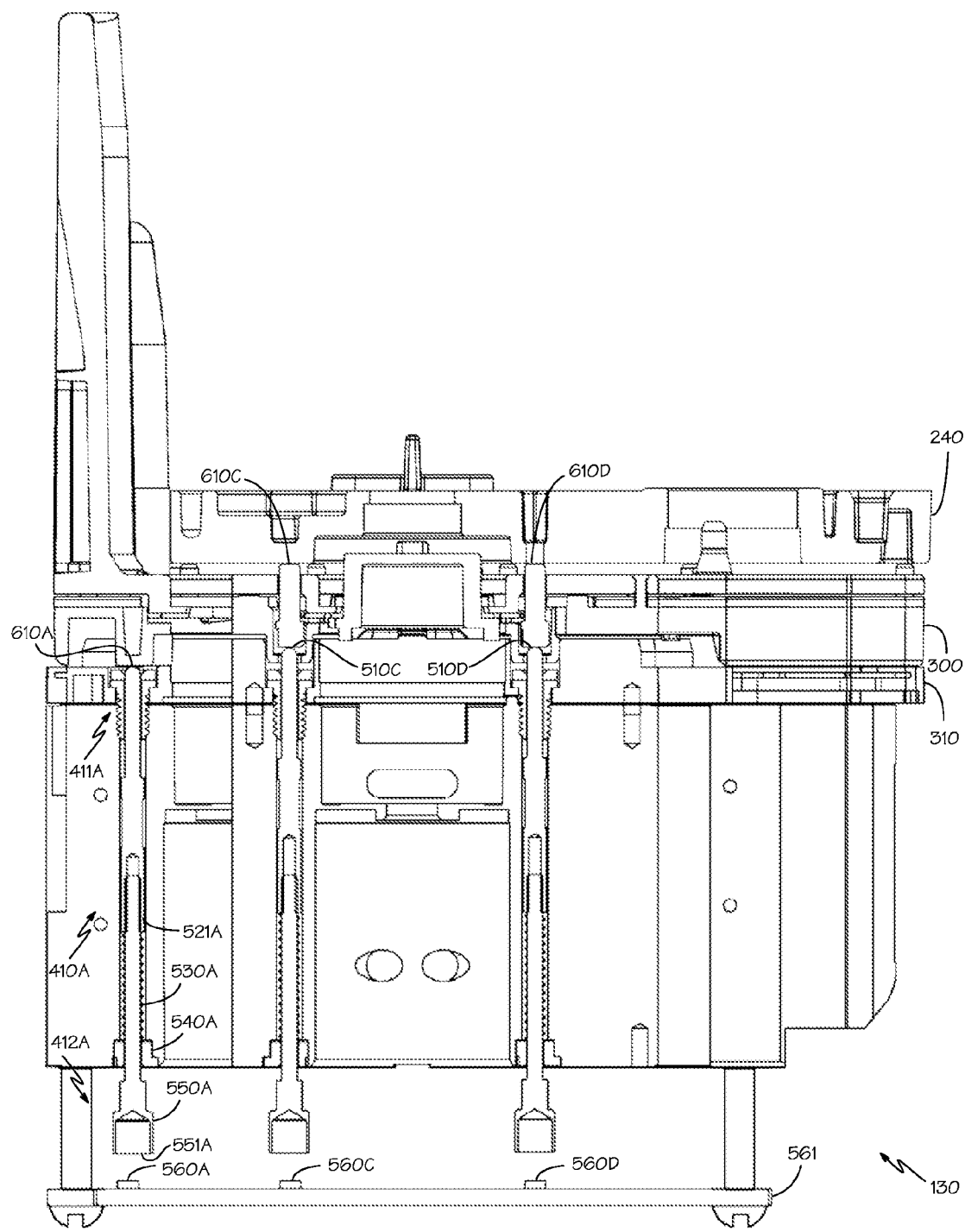
FIG. 6C is a sectional illustration of the plurality of detection pins of the carriage of FIG. 4 relative to the surgical instrument, the ISA and the circuit board upon the engagement of the surgical instrument with the ISA taken along section line 6A-6A in FIG. 4.

As is illustrated in FIGS. 6A-6C, which are section views taken along section line 6A-6A of FIG. 4, some of the detection pins 410A-410B may be shorter in length than others of the detection pins 410C-410D. In one embodiment, the shorter detection pins 410A-410B may be about 1.25 millimeters (0.050 inches) shorter than the longer detection pins 410C-410D, for example.

The circuit board 561, which is mechanically fixed to the instrument carriage 130, includes analog Hall effect sensors 560A-560D (hereinafter referred to as "sensors"), which provide a signal responsive to the distance between the magnets and the sensors 560A-560D. The Hall effect sensors 560A-560D may include circuitry that provides a digital signal based on the analog signal produced by Hall effect. In one embodiment, the distance between the magnets of each of the detection pins 410A-410B enables a determination of whether the ISA 300 is present and engaged with the carriage 130. For example, the sensor 560A may sense the amplitude of the magnetic field generated by the magnet and may provide an output voltage or digital value responsive to the distance between the magnet face of the detection pin 410A and the sensor 560A. As the distance decreases, the output voltage or digital value may increase.

In such an example, the ISA 300 may be considered to be present and fully engaged with the carriage 130 when the output threshold of both of the sensors 560A-560B exceeds a first predetermined threshold.

In such an example, the sensors 560C-560D may determine the distance between the magnets and the sensors 560C-560D. The distance between the magnets of each of the detection pins 410C-410D enables a determination of whether the surgical instrument 120 is present and engaged with the ISA 300.

In one embodiment, the sensors 560A-560D may be calibrated as part of a calibration procedure during the assembly of the instrument carriage 130. As an example, during assembly, a calibration block may be placed on the control surface 310 of the instrument carriage 130 to depress the detection pins 410A-410D a known amount. The output voltage or digital value provided by the sensors 560A-560D upon application of the calibration block may then be stored in a carriage controller 340 and used as a threshold value to determine if the ISA 300 or the surgical instrument 120 is present and engaged.

Referring the FIG. 6A, an exemplary embodiment of the plurality of detection pins 410A-410D of the carriage 130 of FIG. 4 relative to the surgical instrument 120, the ISA 300 and the circuit board 561 prior the engagement of the ISA 300 with the control surface 310 of the carriage 130 is shown. The detection pins 410A-410D are coupled to the instrument carriage 130 which provides the mechanical ground to which motion of the detection pins is referenced. The circuit board 561 and the attached Hall effect sensors 560A-560D are also mechanically fixed to the instrument carriage 130 allowing motion of the detection pins to be referenced to the sensors. The distal end 411A of the detection pin 410A extends from the control surface 310 to the sensing tip 510A. In the embodiment of FIG. 6A, the carriage 130 includes the detection pins 410A-410D, although only the detection pins 410A and 410C-410D are visible. In one embodiment, the detection pins 410A-410B may be used to detect the presence and engagement of the ISA 300 and the detection pins 410C-410D may be used to detect the presence and engagement of the surgical instrument 120.

In FIGS. 6A-6C, the upstops 540A-540D are shown fixed to the instrument carriage 130. Therefore, the upstops 540A-540D provide a fixed point of reference that limits the upward travel of the magnet face 551A away from the sensor 560A to a known distance.

Referring to FIG. 6B, the exemplary embodiment of the plurality of detection pins 410A-410D of the carriage 130 of FIG. 4 relative to the ISA 300 and the circuit board 561 upon the engagement of the ISA 300 with the control surface 310 of the carriage 130 is shown. The ISA 300 includes a flat surface 610A that comes in contact with the sensing tip 510A of the detection pins 410A upon engagement of the ISA 300 with the control surface 310 of the carriage 130. As a result of the engagement of the ISA 300 with the control surface 310 of the carriage 130, a surface of the ISA 300 depresses the detection pins 410A-410B into the carriage wells 420A-420B. As mentioned above, the detection pins 410A-410B may be shorter in length than the detection pins 410C-410D to accommodate the heights of the surfaces they contact on the ISA 300.

The ISA 300 also includes presence pins 610C-610D that are configured to contact the detection pins 410C-410D upon engagement of the ISA 300. As seen in FIG. 6A, the presence pins 610C-610D are in their lowermost position when the ISA 300 is not engaged with the control surface 310 of the carriage 130. Engaging the ISA 300 lifts the presence pins 610C-610D within the ISA as seen in FIG. 6B.

As the detection pins 410A-410B operate in the same manner, the following discussion of FIG. 6B will refer to the operation of the detection pin 410A for simplicity, unless otherwise noted. The depression of the detection pin 410A causes the spring 530A to compress due to force applied from the shoulder 521A of the shaft 5201 applying pressure toward the proximal end 412A of the detection pin 410A. The spring 530A compresses against the upstop 540A, which, as discussed above, is fixed to the carriage 130. As the detection pin 410A is depressed by the engagement of the ISA 300, the detection pin 410A slides through the upstop 540A as the proximal end 412A of the detection pin 410A approaches the sensor 560A. As the proximal end 412A of the detection pin 410A approaches the sensor 560A, the magnetic field produced by the magnet contained in the magnet housing 550A causes the output voltage or digital value of the sensor 560A to increase. When the output voltage or values of both of the sensors 560A-560B, corresponding to the detection pins 410A-410B respectively, exceeds a first predetermined threshold, which may be a threshold set by a calibration process as described above, the ISA 300 is considered to be present and fully engaged with the control surface 310 of the carriage 130.

Referring now to FIG. 6C, the exemplary embodiment of the plurality of detection pins 410A-410D of the carriage 130 of FIG. 4 relative to the surgical instrument 120, the ISA 300 and the circuit board 561 upon the engagement of the surgical instrument 120 with the ISA 300 is shown. As the surgical instrument 120 engages with the ISA 300, the surgical instrument 120 makes contact with and depresses the presence pins 610C-610D. In turn, the depression of the presence pins 610C-610D depresses the detection pins 410C-410D on the control surface 310 of the carriage 130. Upon contacting the detection pins 410C-410D, the presence pins 610C-610D depress the detection pins 410C-410D into the carriage wells 420C-420D.

As the detection pins 410C-410D are depressed by the engagement of the surgical instrument 120 with the ISA 300, the detection pins 410C-410D slide through the upstops 540C-540D, respectively. Subsequently, the proximal ends 412C-412D of each of the detection pins 410C-410D approach the corresponding sensor of the sensors 560C-560D. As the proximal ends 412C-412D of the detection pins 410C-410D approach the sensors 560C-560D, the magnetic fields produced by the magnet faces 551C-551D cause the output voltage or digital values of the sensors 560C-560D to increase. When the output voltage of both of the sensors 560C-560D exceeds a second predetermined threshold, which may be a threshold set by a calibration process as described above, the surgical instrument 120 is considered to be present and fully engaged with the ISA 300.

It will be appreciated that the presence of the ISA or the surgical instrument could be detected by a single detection pin or sensor. Two detection pins or sensors may be used so that partial engagement with the ISA or the surgical instrument at an angle to the receiving surface can be detected. Two detection pins or sensors may also be used to detect inconsistent outputs from the two sensors that may indicate a need for system service.

Figure 7:
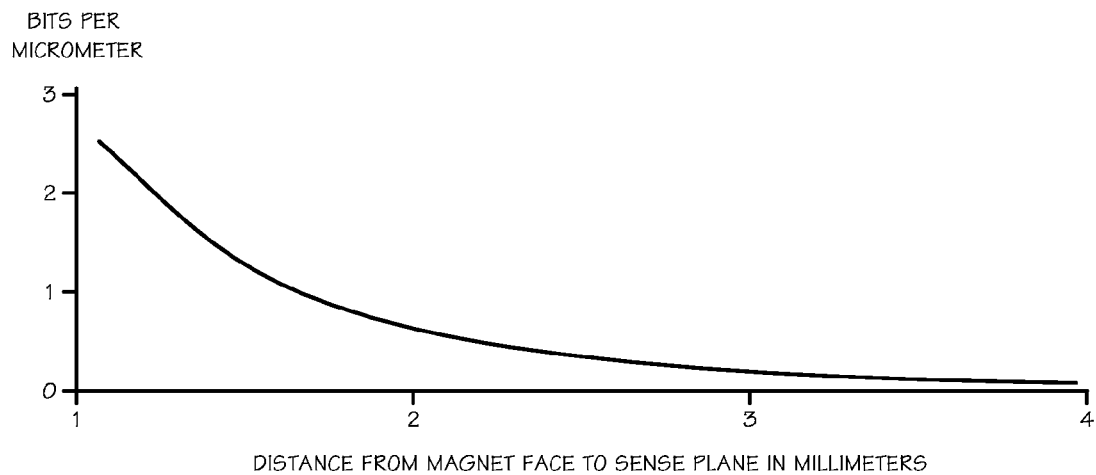
FIG. 7 is a graph showing the digital output of an exemplary analog Hall effect sensor as a function of the distance between a magnet and the analog Hall effect sensor.

FIG. 7 illustrates the response of a digital output from one embodiment of a Hall effect sensor. The sensitivity of an analog Hall effect sensor increases as a magnet moves closer to the sensor. As the distance between the magnet face 551A and the sensor 560A decreases, e.g., the ISA 300 is engaging with the control surface 310 of the carriage 130, the number of bits of resolution per micrometer of travel increases for a sensor with digital output values. For example, for the embodiment of the sensor illustrated, when the distance between magnet face 551A and the sensor 560A is greater than 2 mm., a change of 1 bit in the digital output value represents more than 1 micrometer of travel. When the distance between magnet face 551A and the sensor 560A is less than 1 mm., 1 micrometer of travel will produce a change of more than 1 bit in the digital output value.

Figure 8A:
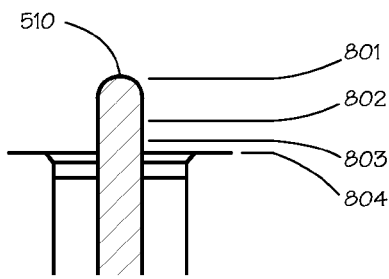
FIGS. 8A-8D illustrate a plurality of depression states for an exemplary embodiment of a detection pin.
Figure 8B:
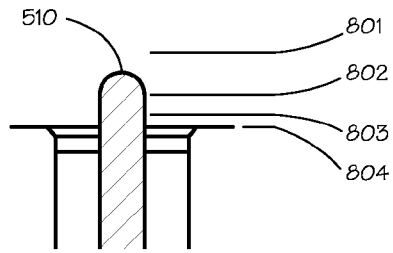
Figure 8C:
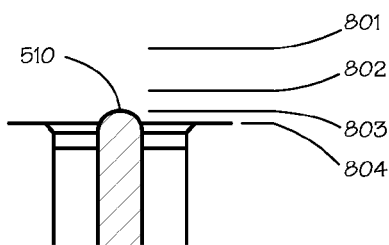
Figure 8D:
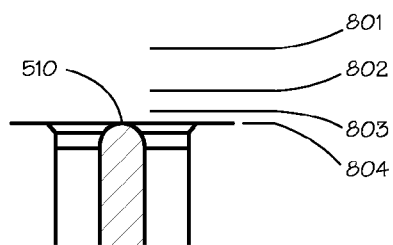

Referring to FIGS. 8A-8D, a plurality of states of the detection pin are shown. FIG. 8A illustrates the sensing tip 510 of the detection pin at an uppermost state, e.g., a first state 801. First state 801 may represent the sensing tip 510 of the detection pin in its uppermost position, which may be termed the first depression point. FIG. 8B illustrates the sensing tip 510 of the detection pin at a second depression point, e.g., a second state 802. FIG. 8C illustrates the sensing tip 510 of the detection pin at a third depression point, e.g., a third state 803. FIG. 8D illustrates the sensing tip 510 of the detection pin at a fourth depression state, e.g., a fourth state 804. It will be seen that the four depression states are increasingly closer together as the magnet face 551A approaches the sensor 560A and the resolution of the output values increases. The four depression states may be chosen such that the difference in output values is approximately equal between each pair of adjacent depression states.

Based on the detection of multiple states, the invention may be implemented using two rather than four detection pins to detect both the ISA 300 and the surgical instrument 120. The detection of multiple states may further allow the detection of different instrument or instrument adapter types, such as distinguishing a surgical instrument from an endoscopic camera.

The second through fourth states 802-804 may represent one or more of (i) a portion of the engagement with the ISA 300 has been completed, (ii) the ISA 300 is fully engaged with the control surface 310 of the carriage 130, (iii) a portion of the engagement process between the surgical instrument 120 and the ISA 300 has been completed, (iv) the engagement process between the surgical instrument 120 and the ISA 300 has been completed, (v) a second surgical instrument, different than the surgical instrument 120, has completed a portion of the engagement process with the ISA 300, and/or (vi) the second surgical instrument has completed the engagement process with the ISA 300. Additionally, one or more of the states may signify that the second surgical instrument, the surgical instrument 120 and/or the ISA 300 are disengaging or have completely disengaged from the control surface 310 of the carriage 130.

As an illustrative example, using only two detection pins, the first state 801 may represent that no contact has been made with the control surface 310 of the carriage 130. In one embodiment, upon contact with the detection pins 410C-410D, the presence pins 610C-610D are raised to an uppermost position within the ISA 300. As the ISA 300 engages with the control surface 310 of carriage 130, the presence pins 610C-610D may reach the upward limit of their travel within the ISA and depress the detection pins 410A-410B to the second state 802. When both of the detection pins are at the second state 802, the ISA 300 may be present and fully engaged with the control surface 310 of the carriage 130.

As the surgical instrument 120 engages with the ISA 300, the surgical instrument 120 makes contact with and depresses the presence pins 610C-610D. In turn, the depression of the presence pins 610C-610D depresses the detection pins 410C-410D on the control surface 310 of the carriage 130. When both of the detection pins are at the third state 803, the surgical instrument 120 may be present and fully engaged with the ISA 300. When both of the detection pins are at the fourth state 804, a second type of surgical instrument may be present and fully engaged with the ISA 300.

Additionally, in one embodiment, the surgical instrument 120 may include a radio-frequency identification (RFID) tag. In such an embodiment, upon beginning an engagement process, the RFID tag may provide the teleoperated actuated surgical instrument manipulator with identifying information of the surgical instrument 120. Such identifying information may be used to determine which state of the detection pins, as discussed above, is necessary to consider the surgical instrument 120 as fully engaged with the ISA 300. For example, the teleoperated actuated surgical instrument manipulator may read the RFID tag of the surgical instrument 120 to require the detection pins 410C-410D to be depressed for at least a first predetermined amount of time at the third state 803 to conclude the surgical instrument 120 is engaged with the ISA 300. Alternatively, the teleoperated actuated surgical instrument manipulator may read the RFID tag of the second surgical instrument to require the detection pins 410C-410D to be depressed for at least a second predetermined amount of time at the fourth state 804 to conclude the second surgical instrument is engaged with the ISA 300. Herein, the first predetermined amount of time and the second predetermined amount of time may or may not be equivalent in length.

Removal of the Surgical Instrument and the Instrument Sterile Adapter

As with the installation of the surgical instrument 120, when removing the surgical instrument 120, readings may be taken from both of the detection pins 410C-410D. In one embodiment, both sensors 560C-560D are required to provide an output voltage below a third threshold to determine that the surgical instrument has been removed. The third threshold may be set as a predetermined amount less than the second threshold used to determine the presence of the surgical instrument. The difference between the second and third thresholds may provide a hysteresis effect in which a detection pin that has detected the presence of the surgical instrument has to move a significant distance upward before detecting the removal of the surgical instrument.

In one embodiment, the removal of the surgical instrument 120 may be detected by the teleoperated actuated surgical instrument manipulator using a three-phase system. First, the teleoperated actuated surgical instrument manipulator detects the change in output voltage from the sensors 560C-560D. Second, the surgical instrument 120 may include a RFID tag, as discussed above. As the surgical instrument 120 disengages from the control surface 310 of the carriage 130 and moves away from the teleoperated actuated surgical instrument manipulator, the teleoperated actuated surgical instrument manipulator will eventually no longer be able to detect the RFID tag. Third, the surgical instrument 120 may include a magnet. Subsequent to the inability of the teleoperated actuated surgical instrument manipulator to detect the RFID tag, as the surgical instrument 120 is moved away from the control surface 310 of the carriage 130, the teleoperated actuated surgical instrument manipulator will eventually no longer be able to detect the magnet. Therefore, in an embodiment employing a three-phase detection system, the teleoperated actuated surgical instrument manipulator will determine the surgical instrument 120 has been removed from the surgical instrument manipulator only upon detecting (i) the change in output voltage by both sensors 560C-560D below a third threshold, (ii) the inability to read the RFID tag of the surgical instrument 120, and (iii) the inability to detect the magnet of the surgical instrument 120.

Additionally, the detection of the removal of the ISA 300 is performed in a similar manner. The teleoperated actuated surgical instrument manipulator detects a change in the output voltage of the sensors 560A-560B. When both of the sensors 560A-560B provide an output voltage below a fourth threshold, the teleoperated actuated surgical instrument manipulator may determine the ISA 300 has been completely disengaged and removed from the control surface 310 of the carriage 130. As discussed in connection with the second and third thresholds for the surgical instrument detection, a difference between the first and fourth thresholds may provide hysteresis in detecting the presence and removal of the ISA. As discussed above, the surgical instrument 120 may utilize a RFID tag in the detection of the removal process. Similarly, the ISA 300 may include a RFID tag for utilization in the removal process as well.

The plurality of thresholds stated above are not necessarily all equivalent nor are one or more of the plurality of thresholds necessarily equivalent. However, all of the thresholds may be equivalent in one embodiment, one or more may be equivalent in a second embodiment, and all may be different in a third embodiment.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. An instrument carriage for providing control of a surgical instrument attached to the instrument carriage, the instrument carriage comprising:
    a control surface that attaches to the surgical instrument to provide control of the surgical instrument;
    a first detection pin coupled to the instrument carriage, the first detection pin having a first distal end that extends from the control surface;
    a first magnet fixed to a first proximal end of the first detection pin;
    a carriage controller;
    a circuit board fixed to the instrument carriage;
    a first Hall effect sensor fixed to the circuit board facing the first magnet, the first Hall effect sensor providing a first output signal that is communicatively coupled to the carriage controller, the carriage controller providing an indication that the surgical instrument is present on the instrument carriage when movement of the first detection pin causes the first output signal to exceed a first instrument presence threshold value that is stored in the carriage controller as part of a calibration procedure during assembly of the instrument carriage.

2. The instrument carriage of claim 1 wherein the carriage controller provides an indication that an instrument sterile adapter (ISA) is present on the instrument carriage when movement of the first detection pin causes the first output signal to exceed a first ISA threshold value that is stored in the carriage controller as part of the calibration procedure during assembly of the instrument carriage.

3. The instrument carriage of claim 1 wherein an instrument sterile adapter is attached to the instrument carriage and the surgical instrument is attached to the instrument carriage through the instrument sterile adapter, the instrument sterile adapter including a first presence pin to extend the first distal end of the first detection pin.

4. The instrument carriage of claim 1 wherein the carriage controller provides an indication that the surgical instrument is removed from the instrument carriage when movement of the first detection pin causes the first output signal to be less than a first instrument removal threshold value that is less than the first instrument presence threshold value.

5. The instrument carriage of claim 1 wherein the control surface includes a well and the first distal end is within the well to protect the first detection pin from horizontal forces.

6. The instrument carriage of claim 1 further comprising:
a second detection pin coupled to the instrument carriage, the second detection pin having a second distal end that extends from the control surface spaced apart from the first distal end;
a second magnet fixed to a second proximal end of the second detection pin;
a second Hall effect sensor fixed to the circuit board facing the second magnet, the second Hall effect sensor providing a second output signal that is communicatively coupled to the carriage controller, the carriage controller providing the indication that the surgical instrument is present on the instrument carriage further requires movement of the second detection pin causing the second output signal to exceed a second instrument presence threshold value that is stored in the carriage controller as part of the calibration procedure during assembly of the instrument carriage.

7. A method for detecting presence of a surgical instrument coupled to an instrument carriage, the method comprising:
receiving a first output signal from a first sensor fixed in position relative to the instrument carriage, the first output signal being responsive to motion of a first detection pin created by presence of the surgical instrument;
calibrating the first sensor by depressing the first detection pin a first known distance and storing a first instrument presence threshold value according to the first output signal; and
indicating that the surgical instrument is present on the instrument carriage when movement of the first detection pin causes the first output signal to exceed the first instrument presence threshold value.

8. The method of claim 7 further comprising:
storing a first ISA threshold value that is less than the first instrument presence threshold value; and
indicating that an instrument sterile adapter (ISA) is present on the instrument carriage when movement of the first detection pin causes the first output signal to exceed the first ISA threshold value.

9. The method of claim 7 further comprising:
attaching an instrument sterile adapter to the instrument carriage to receive the surgical instrument; and
extending a first distal end of the first detection pin with a first presence pin that is loosely held within the instrument sterile adapter.

10. The method of claim 7 further comprising indicating that the surgical instrument is removed from the instrument carriage when movement of the first detection pin causes the first output signal to be less than a first instrument removal threshold value that is less than the first instrument presence threshold value.

11. The method of claim 7 further comprising protecting the first detection pin from horizontal forces by locating a first distal end of the first detection pin within a well.

12. The method of claim 7 further comprising:
receiving a second output signal from a second sensor fixed in position relative to the instrument carriage, the second output signal being responsive to motion of a second detection pin created by presence of the surgical instrument;
calibrating the second sensor by depressing the second detection pin a second known distance and storing a second instrument presence threshold value according to the second output signal; and
indicating that the surgical instrument is present on the instrument carriage only when movement of the second detection pin causes the second output signal to exceed the second instrument presence threshold value in addition to the first output signal exceeding the first instrument presence threshold value.

13. The method of claim 7 wherein calibrating the first sensor further comprises depressing the first detection pin a third known distance and storing a third instrument presence threshold value according to the first output signal, and the method further comprises indicating an additional state of the surgical instrument when movement of the first detection pin causes the first output signal to be more than the third instrument presence threshold value.

14. The instrument carriage of claim 1 wherein the carriage controller provides an indication of an additional state of the surgical instrument when movement of the first detection pin causes the first output signal to exceed a third instrument presence threshold value that is stored in the carriage controller as part of the calibration procedure during assembly of the instrument carriage.

15. An instrument carriage for providing control of a surgical instrument attached to the instrument carriage, the instrument carriage comprising:
a control surface that attaches to the surgical instrument to provide control of the surgical instrument;
a first detection pin coupled to the instrument carriage, the first detection pin having a first distal end that extends from the control surface;
a first magnet fixed to a first proximal end of the first detection pin;
means for providing an indication that the surgical instrument is present on the instrument carriage responsive to movement of the first detection pin.

16. The instrument carriage of claim 15 wherein the means for providing an indication further provides an indication that an instrument sterile adapter (ISA) is present on the instrument carriage responsive to movement of the first detection pin.

17. The instrument carriage of claim 15 wherein the means for providing an indication further provides an indication that the surgical instrument is removed from the instrument carriage responsive to movement of the first detection pin.

18. The instrument carriage of claim 15 wherein the means for providing an indication further provides an indication of an additional state of the surgical instrument responsive to movement of the first detection pin.

* * * * *